United States Patent [19]

Kobylecki et al.

[11] 4,241,067
[45] Dec. 23, 1980

[54] 14-AMINO DERIVATIVES OF MORPHINE, METHODS OF MAKING THEM AND ANALGESIC COMPOSITIONS CONTAINING THEM

[75] Inventors: Ryszard J. Kobylecki, Patrington; Ian G. Guest, Burstwick; John W. Lewis, North Ferriby, all of England; Gordon W. Kirby, Glasgow, Scotland

[73] Assignee: Reckitt & Colman Products Limited, London, England

[21] Appl. No.: 886,834

[22] Filed: Mar. 15, 1978

[30] Foreign Application Priority Data

Mar. 23, 1977 [GB] United Kingdom ............... 12342/77

[51] Int. Cl.$^3$ .................. A61K 31/485; C07D 489/06
[52] U.S. Cl. .................................... 424/260; 546/44; 546/45; 542/403
[58] Field of Search ........................ 260/285; 424/260; 542/403; 546/44, 45

[56] References Cited

U.S. PATENT DOCUMENTS

| | | | |
|---|---|---|---|
| 3,819,635 | 6/1974 | Pachter et al. | 260/285 |
| 4,017,497 | 4/1977 | Lim et al. | 260/285 |

OTHER PUBLICATIONS

Bentley et al., Chemical Communications, (1969), p. 1411.
Allen et al., Chemical Communications, (1970), p. 1346.
Fieser et al., "Reagents for Organic Synthesis", John Wiley & Sons, N.Y. (1967), pp. 1081-1082.
Joshi et al., Chemical Abstracts, vol. 43, 7438c(1949).
Arnold, Chemical Abstracts, vol. 78, 98250q (1973).
Allen; R. M., "Synthesis of New Codeinone and Indolinocodeinone Derivatives", Thesis submitted to Loughborough University of Technology, 9/71, cited in Index to Theses, vol. XXII, 1971-1972, ed Paterson et al., Aslib, London (1974).
Rice, Journal of Medicinal Chemistry, vol. 20, No. 1, pp. 164-165, (1/77).

*Primary Examiner*—Jose Tovar
*Assistant Examiner*—Diana G. Rivers
*Attorney, Agent, or Firm*—Bacon & Thomas

[57] ABSTRACT

Novel derivatives of morphine having the general formula:

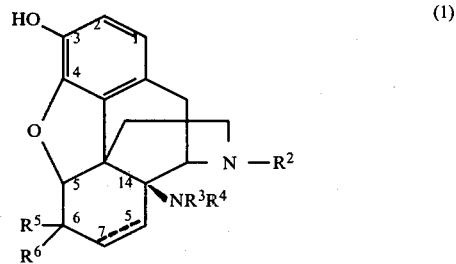

wherein $R^2$, $R^3$, $R^4$, $R^5$ and $R^6$ are certain specified values, and their pharmaceutically acceptable salts.

The compounds exhibit activity in the central nervous system and may be presented in the form of pharmaceutical compositions comprising a compound of formula (I), or a pharmaceutically acceptable salt thereof, in association with a pharmaceutically acceptable diluent or carrier.

17 Claims, No Drawings

14-AMINO DERIVATIVES OF MORPHINE, METHODS OF MAKING THEM AND ANALGESIC COMPOSITIONS CONTAINING THEM

This invention relates to derivatives of morphine, to processes for their preparation and to pharmaceutical compositions thereof.

According to this invention there are provided compounds of the formula:

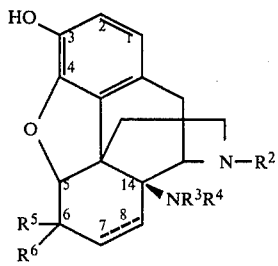

wherein $R^2$ is methyl or Ar-alkyl $C_{1-5}$;

$R^3$ is hydrogen, alkyl $C_{1-12}$ preferably alkyl $C_{5-8}$, alkenyl $C_{3-8}$, cycloalkyl $C_{3-7}$ alkyl $C_{1-4}$, Ar-alkyl $C_{1-5}$ or Ar-alkenyl $C_{3-5}$, provided that $R^3$ does not contain the system —CH=CH— attached to the nitrogen atom at position 14;

$R^4$ is hydrogen, alkyl $C_{1-8}$ or the group $COR^7$ in which $R^7$ is hydrogen, alkyl $C_{1-11}$, alkenyl $C_{2-7}$, Ar, Ar-alkyl $C_{1-5}$, Ar-alkenyl $C_{2-5}$, cycloalkyl $C_{3-8}$ or cycloalkyl $C_{3-8}$ alkyl $C_{1-3}$;

Ar is phenyl or phenyl substituted by halogen, alkyl $C_{1-3}$, hydroxy or alkoxy $C_{1-3}$;

$R^5$ is hydrogen and $R^6$ is hydroxy; or $R^5$ and $R^6$ are together oxygen;

the dotted line indicates an optional bond; and their pharmaceutically acceptable salts.

Suitable values of $R^2$ contemplated by the invention include methyl and phenethyl.

Suitable values of $R^3$ contemplated by the invention include hydrogen, methyl, ethyl, propyl, butyl, pentyl, hexyl, heptyl, octyl, nonyl, decyl, dodecyl, allyl, 3-methallyl, 3,3-dimethallyl, cyclopropylmethyl, cyclobutylmethyl, cyclopropylethyl, benzyl, α-phenethyl, β-phenethyl, 3-phenpropyl and 4-phenbutyl.

Suitable values of $R^4$ include hydrogen, methyl, ethyl, propyl, formyl, acetyl, propionyl, butyryl, pentanoyl, hexanoyl, heptanoyl, octanoyl, cinnamoyl, phenylacetyl, 3-phenpropionyl, 4-phenylbutyryl, cyclopropyl carbonyl and cyclobutylcarbonyl.

Halogen includes fluorine, chlorine, bromine and iodine.

The invention also provides pharmaceutical compositions comprising a compound of Formula I or a pharmaceutically acceptable salt thereof in association with a pharmaceutically acceptable diluent or carrier.

The compounds of Formula I may be converted to a pharmaceutically acceptable non-toxic acid addition salt by treatment with an appropriate acid, for example, an inorganic acid, such as hydrochloric, sulphuric or phosphoric acid; or an organic acid, such as, acetic, propionic, malonic, succinic, fumaric, tartaric, citric, benzoic, or cinnamic acid.

The 14-β-amino morphines of Formula I exhibit activity in animal tests methods. In particular the compounds exhibit activity in the central nervous system.

The compounds of Formula I may be prepared from the compounds of Formula II:

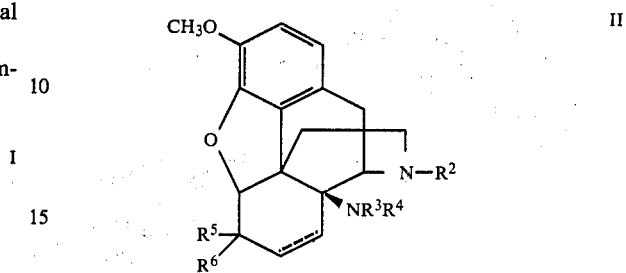

in which $R^2$, $R^3$, $R^4$, $R^5$, $R^6$ and the dotted line are as hereinbefore defined, by treatment with boron tribromide or boron trichloride. The reaction is conveniently carried out in the presence of a chlorinated aliphatic hydrocarbon such as chloroform, carbon tetrachloride, tetrachloroethylene, or hexachloroethane and most conveniently in methylene chloride, at a temperature −50° to 0° and preferably −30° to −10° C.

The compounds of Formula I in which $R^5$ and $R^6$ are together oxygen may also be prepared from the compounds of Formula II in which $R^3$ and $R^4$ are as hereinbefore defined and both $R^5$ and $R^6$ are methoxy by similar treatment with boron tribromide or boron trichloride.

The compounds of Formula I in which $R^3$ and/or $R^4$ are other than hydrogen may also be prepared from the analogous compounds of Formula I in which $R^3$ and/or $R^4$ are hydrogen by standard methods of alkylation with an organo halide $R^8X$ (where $R^8$ has the same values as $R^3$ other than hydrogen, and X is chlorine, bromine or iodine) or by acylation with an acyl anhydride $(R^7CO)_2O$ or chloride $R^7COCl$ (where $R^7$ is as hereinbefore defined).

The compounds of Formula I in which the optional bond is absent may be prepared from analogous compounds of Formula I in which the optional bond is present by hydrogenation in the presence of a catalyst such as 10% palladium on carbon, carrying out the reduction in a solvent such as ethyl acetate, methylene chloride or a lower alcohol such as methanol, ethanol or isopropanol.

The compounds of Formula I in which $R_5$ is hydrogen and $R^6$ is hydroxy may also be prepared from the analogous compounds of Formula I in which $R^5$ and $R^6$ are together oxygen by treatment with sodium borohydride in a lower alcohol such as methanol or ethanol.

The compound of Formula I in which $R^3=R^4=H$, $R^5$ and $R^6$ are together oxygen, and the optional bond is present i.e. the compound 14-β-aminomorphinone may also be prepared by treating 14-β-nitrocodeinone (or its dimethyl ketal) in methylene chloride with boron tribromide or boron trichloride at −50° to 0° C. preferably −30° to −10° C., and reducing the resultant 14-β-nitromorphinone with for example sodium dithionite.

The compounds of Formula II in which $R^2$ is methyl, $R^5$ and $R^6$ are together oxygen or both $R^5$ and $R^6$ are methoxy, and the optional bond is present may be prepared according to the following reaction scheme and obvious variations thereof:

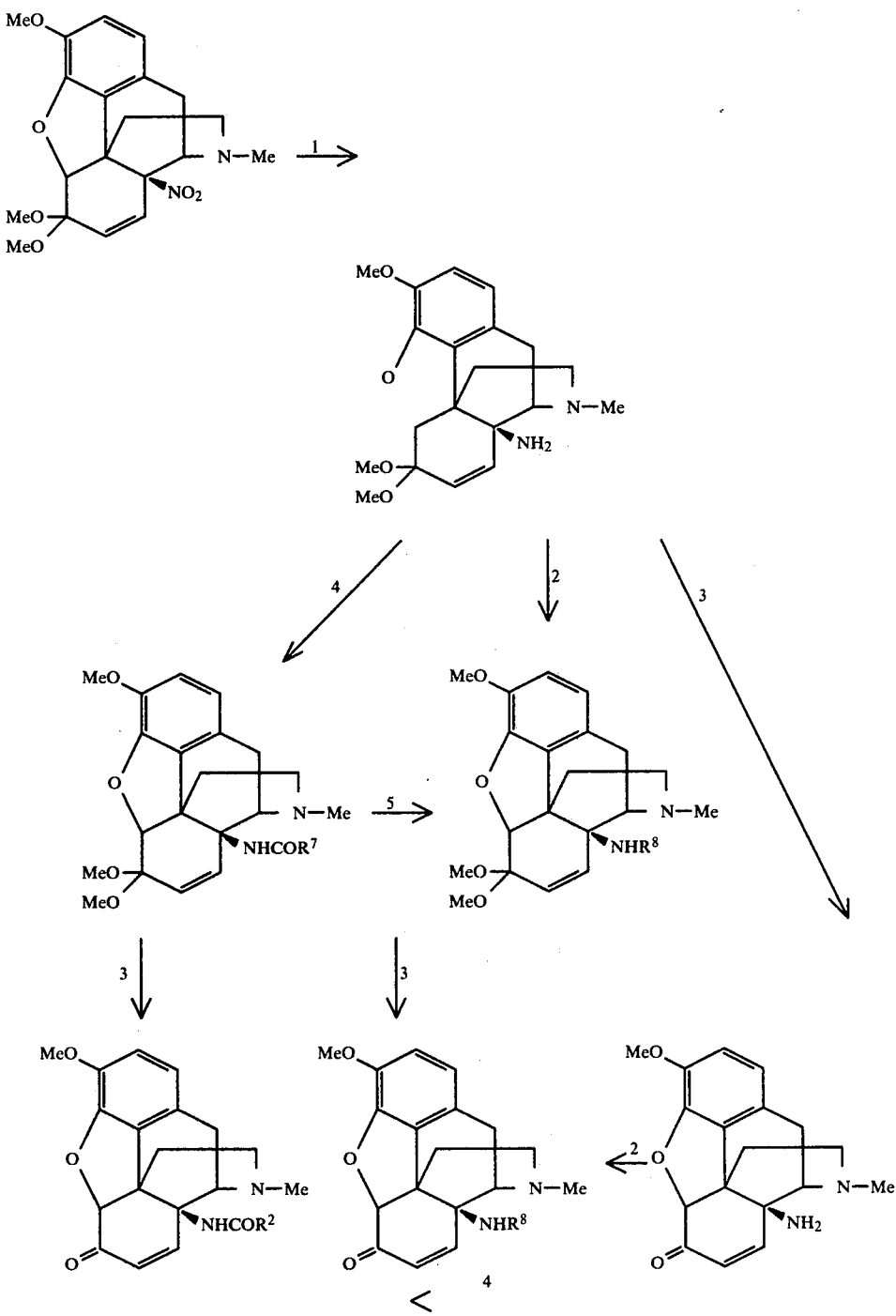

In the reaction scheme in the first stage (reaction 1) 14-β-nitrocodeinone dimethyl ketal is reduced with ammonium chloride and zinc powder in methanol to afford 14-β-aminocodeinone. In further stages of the scheme the conversion of ketal to a ketone (reaction 3) may be carried out by treatment with an aqueous mineral acid such as hydrochloric acid. The amino group may be alkylated (reaction 2) by treatment with an organo halide such as cyclopropylmethyl bromide conveniently in aqueous acetone in the presence of sodium bicarbonate and potassium iodide. The amino group may be acylated (reaction 4) by standard methods such as acid chloride/pyridine, acid chloride/triethylamine/-chloroform, acid chloride/sodium bicarbonate/water/-chloroform or acid anhydride/pyridine. The acyl compounds where $R^5 = R^6 =$ methoxy may be reduced (reaction 5) by treatment with for example lithium aluminium hydride in tetrahydrofuran.

The compounds of Formula II in which the optional bond is absent may be prepared from the analogous compounds of Formula II in which the optional bond is present by catalytic reduction using the method as described above in the similar transformation with the compounds of Formula I. Similarly compounds of Formula II in which $R^5$ is hydrogen and $R^6$ is hydroxy, may be prepared by the same techniques to those described above for the analogous compounds of Formula I.

The compounds of Formula II in which $R^2$ is Aralkyl $C_{1-5}$ may be prepared by analogous methods to those described above for the compounds of Formula II in which $R^2$ is methyl.

The compounds of Formula II in which $R^2$ is hydrogen may be prepared by removing N-protecting groups from analogous compounds of Formula II in which $R^2$ is —COY, where Y is hydrogen, alkyl $C_{1-6}$, alkoxy $C_{1-6}$, phenoxy, benzyloxy or $\beta,\beta,\beta$,-trichloroethoxy, by standard methods for the removal of N-protecting groups. These compounds of Formula II in which $R^2$ is COY may be prepared by analogous methods to those described above for the compounds of Formula II in which $R^2$ is methyl. Suitable methods for removing the benzyloxycarbonyl group include catalytic hydrogenolysis and the use of HBr/acetic acid, boron tribromide or trifluoroacetic acid. Phenoxycarbonyl may be removed using hydrazine hydrate. It will be appreciated that since these reagents may cause transformation in other parts of the molecule the selection of the most suitable of the reagents for deprotection will be dependent upon the final compound envisaged. In turn the selection of the protecting group will be dependent upon which deprotecting agent may be used.

The invention is illustrated by the following non-limiting Examples in which temperatures are in degrees centigrade. Examples 1 to 76 describe the preparation of intermediates and Examples 77 to 153 the preparation of compounds of the invention.

EXAMPLE 1

14-β-Aminocodeinone

14-β-Nitrocodeinone dimethyl ketal (800 mg) was dissolved in hot absolute methanol (100 ml) and the solution treated with ammonium chloride (1.25 g) and zinc powder (1.25 g) and the mixture heated under reflux with stirring for 1½ hours. The hot reaction mixture was filtered and the filtrate evaporated in vacuo and the residue dissolved in chloroform and passed through a column of grade III alumina. The column was eluted with chloroform and combined eluents evaporated in vacuo and the residue recrystallised from aqueous methanol to give 14-β-aminocodeinone dimethyl ketal as colourless needles (0.58 g, 79%) m.p. 133°–4°. A solution of the ketal in dilute hydrochloric acid was allowed to stand at room temperature for two hours and the pH was adjusted to 7.0 with sodium bicarbonate and extracted with chloroform. The combined extracts were dried and the solvent removed in vacuo to give 14-β-aminocodeinone as colourless needles from petrol ether (b.p. 80°–100°), m.p. 193°–4°.

EXAMPLE 2

14-β-Methylaminocodeinone (a) A solution of 14-β-aminocodeinone dimethyl ketal (2.6 g) in chloroform (100 ml) was treated with sodium bicarbonate (5 g) and water (50 ml). To the stirred mixture was added ethyl chloroformate (0.9 g) dropwise and the mixture stirred at room temperature for a further 30 minutes. The organic layer was separated and the aqueous phase extracted with chloroform and the combined extracts were dried and evaporated in vacuo. The residual oil as adsorbed onto grade III alumina and eluted with chloroform and the combined eluents evaporated in vacuo. The residual oil was dissolved in anhydrous tetrahydrofuran (15 ml) and added dropwise to a stirred suspension of lithium aluminium hydride (1.0 g) in tetrahydrofuran (40 ml) and the mixture stirred at room temperature for 30 minutes and under reflux for a further 2 hours. The excess lithium aluminium hydride was decomposed with saturated sodium sulphate solution and the suspension filtered and the solid washed with chloroform. The combined filtrates, were washed with water, dried and evaporated in vacuo and the residual oil dissolved in excess dilute hydrochloric acid and allowed to stand at room temperature for 2 hours. The pH was adjusted to 7.0 with sodium bicarbonate and extracted with chloroform and the combined extracts washed with water, dried and evaporated. The residue was recrystallised from ether-petroleum ether to give 14-β-methylaminocodeinone as colourless needles (0.90 g, 38%), m.p. 157°–8°.

(b) A solution of 14-β-aminocodeinone dimethyl ketal (3.0 g) in 10% aqueous acetone (100 ml) was treated with sodium bicarbonate (5.0 g), methyl iodide (2.38 g) and heated to reflux for 3.5 hours. The acetone was removed in vacuo, and the residue dissolved in dilute hydrochloric acid and allowed to stand at room temperature for 2 hours. The solution was filtered to remove a small amount of insoluble material, the pH adjusted to 7.0 with sodium bicarbonate, extracted with methylene chloride, and the organic extracts were washed with water, dried, and evaporated. The desired material was separated from the mixture of products by chromatography on silica gel (chloroform/10% methanol). 14-β-Methylaminocodeinone (0.51 g) was obtained as colourless needles by recrystallisation from petroleum ether (b.p. 60°–80°), m.p. 158°–9°.

EXAMPLE 3

14-β-Ethylaminocodeinone

A solution of 14-β-aminocodeinone dimethyl ketone (4.0 g) in dry pyridine (20 ml) was cooled to 0°, treated with acetyl chloride (6 ml), and the mixture allowed to return to room temperature over 1 hour. Volatiles were removed in vacuo and the residue partitioned between chloroform and dilute sodium hydroxide solution. The organic extracts were separated, dried, and evaporated to give an oil, which was passed down a short column of grade III alumina in chloroform, and the eluents evaporated to give a foam. This foam was dissolved in dry THF (50 ml) and added dropwise over 5 minutes to a suspension of LiAlH$_4$ (2.0 g) in dry THF (30 ml) and the mixture heated to reflux for 2 hours. A saturated aqueous solution of sodium sulphate was added dropwise to the cooled reaction mixture to decompose excess LiAlH$_4$, and precipitated aluminium salts were removed by filtration, and washed thoroughly with chloroform. The organic extracts were washed with water, dried, and evaporated. The resulting oil was dissolved in dilute hydrochloric acid, allowed to stand at room temperature for two hours, the pH adjusted to 7.0 with sodium bicarbonate and the mixture extracted with chloroform. The combined extracts were washed with water, dried, and evaporated to give an oil, which was passed down a short column of grade III alumina in chloroform, and the eluents evaporated to give 14-β-ethylaminocodeinone (1.59 g, 41.8%) as colourless needles from petrol ether (60°–80°), m.p. 226.5°–228°.

EXAMPLE 4

14-β-Octylaminocodeinone

A solution of 14-β-aminocodeinone dimethyl ketal (5.0 g) in chloroform (100 ml) and triethylamine (5 ml) was cooled to 0°, treated with octanoyl chloride (2.5 g) and allowed to warm to room temperature over 1 hour. The solvents were removed by evaporation, the product dissolved in diethyl ether, the ionic salts removed by filtration, and the ether removed in vacuo to give a colourless crystalline solid which was recrystallised from petrol ether (b.p. 40°–60°) to give 14-β-octanoylaminocodeinone dimethyl ketal as colourless crystals, m.p. 89°–90.5°. This was added portionwise over 5 minutes to a cooled suspension of LiAlH$_4$ (2.5 g) in dry THF (60 ml), and the mixture was allowed to warm to room temperature and was then stirred at room temperature overnight. Excess LiAlH$_4$ was destroyed by the dropwise addition of a saturated aqueous solution of sodium sulphate, the aluminium salts removed by filtration, washed well with chloroform, and the organic extracts washed with water, dried, and the solvent removed in vacuo. The resulting oil was dissolved in a mixture of chloroform (50 ml) and dilute hydrochloric acid (65 ml), and allowed to stand at room temperature for 2 hours. The pH was adjusted to 7.0 with sodium bicarbonate and the mixture extracted with chloroform, the combined extracts washed with water, dried and the solvents removed in vacuo. The resulting oil was passed down a short column of grade III alumina in chloroform, and the eluents evaporated in vacuo. This product failed to crystallise and was converted to its hydrochloride salt by addition of a solution of dry HCl in diethyl ether and was recrystallised from an acetone/methanol/diethyl ether mixture to give 14-β-octylaminocodeinone HCl (1.83 g) as pale yellow crystals m.p. 164°–7°.

EXAMPLE 5

14-β-Cyclopropylmethylaminocodeinone (a) A solution of 14-β-aminocodeinone dimethyl ketal (3.0 g) in 10% aqueous acetone (50 ml) was treated with potassium iodide (10 g), sodium bicarbonate (10 g), heated to reflux, treated with cyclopropylmethyl bromide (1.0 g) and heated under gentle reflux for 5 hours. The acetone was removed in vacuo and the residue diluted with water, extracted with chloroform and the combined extracts dried and evaporated to give a residual oil which was dissolved in dilute hydrochloric acid and allowed to stand at room temperature for two hours. The pH was adjusted to 7.0 with sodium bicarbonate, the mixture extracted with chloroform, and the combined extracted dried and evaporated. The residual oil was adsorbed onto grade I basic alumina, eluted with chloroform isolating 14-β-cyclopropylmethylaminocodeinone (1.78 g, 58%) as the least polar component by recrystallisation from petrol ether (60°–80°), m.p. 148°–150°.

(b) Reduction of 14-β-cyclopropylcarbonylaminocodeinone dimethyl ketal (prepared by the general method of Example 3) with LiAlH$_4$, followed by acid hydrolysis using the same general procedure also gave 14-β-cyclopropylmethylaminocodeinone.

EXAMPLE 6

14-β-Formylaminocodeinone

A solution of 14-β-aminocodeinone dimethyl ketal (2.0 g) in 95% formic acid (10 ml) was heated at 55° for 6 hours with stirring. The cooled reaction mixture was poured into excess sodium bicarbonate and extracted with methylene chloride. The combined extracts were washed with water, dried and the solvent removed in vacuo to give an oil, which was adsorbed onto grade III alumina and eluted with chloroform. The eluents were evaporated in vacuo and the residual solid recrystallised from dichloromethane/petroleum ether (b.p. 60°–80°) to give 14-β-formylaminocodeinone (1.39 g, 73.5%) as colourless needles, m.p. 255°–6°.

EXAMPLE 7

14-β-Acetylaminocodeinone

Acetic anhydride (1 ml) was added to a solution of 14-β-aminocodeinone (0.164 g) in dry pyridine (2 ml) and the mixture allowed to stand at room temperature for 12 hours. The volatiles were removed in vacuo and the residue diluted with excess sodium bicarbonate solution and extracted with chloroform. The combined extracts were dried and evaporated in vacuo and the resultant solid recrystallised from methanol to give 14-β-acetylaminocodeinone (0.174 g, 94%) as colourless needles, m.p. 257°–8°.

EXAMPLE 8

14-β-Butyrylaminocodeinone

A solution of 14-β-aminocodeinone dimethyl ketal (4.0 g) in pyridine (20 ml) was cooled to 0°, treated with butyryl chloride (6 ml), and the mixture allowed to warm to room temperature over 1 hour. The volatiles were removed in vacuo, and the residue dissolved in a mixture of chloroform (50 ml) and dilute hydrochloric acid (50 ml) and allowed to stand overnight. The pH was adjusted to 7.0 with sodium bicarbonate and the mixture extracted with chloroform. The combined extracts were washed with water, dried, and the solvent removed in vacuo. The residue was passed down a short column of grade III alumina, and the eluents evaporated. The residual solid was recrystallised from petrol ether (b.p. 60°–80°) to give 14-β-butyrylaminocodeinone (0.58 g) as colourless needles, m.p. 229°–231°.

EXAMPLE 9

14-β-Cinnamoylaminocodeinone

A solution of 14-β-aminocodeinone dimethyl ketal (2.0 g) in chloroform (100 ml) was treated first with a solution of sodium bicarbonate (10 g) in water (100 ml) and then with cinnamoyl chloride (from cinnamic acid [5 g]) and the mixture stirred overnight at room temperature. The organic layer was separated, treated with concentrated hydrochloric acid and allowed to stand at room temperature for 2 hours. The mixture was basified with dilute sodium hydroxide solution and allowed to stand at room temperature for 30 minutes. The organic layer was separated, dried and evaporated in vacuo and the residue purified by chromatography on grade I alumina with chloroform elution followed by recrystallisation from methanol to give 14-β-cinnamoylaminocodeinone (1.85 g, 75%), as colourless tablets, m.p. 273°–5°.

EXAMPLE 10

14-β-Amino-7,8-dihydrocodeinone dimethyl ketal

A solution of 14-β-aminocodeinone dimethyl ketal (4 g) in dry methanol (500 ml) was hydrogenated at atmospheric pressure over 10% Pd/C (1 g). The catalyst was removed by filtration and the solvent removed in vacuo to give an oil which was dissolved in methylene chloride and passed down a short column of grade III alumina and the eluents evaporated in vacuo. The resultant oil crystallised on addition of pentane and the solid was recrystallised from pentane to give 14-β-amino-7,8-dihydrocodeinone dimethyl ketal (3.2 g, 79.6%), as a colourless crystalline solid, m.p. 89°–90.5°.

EXAMPLE 11

14-β-acetylamino-7,8-dihydrocodeinone

This material was prepared from 14-β-amino-7,8-dihydrocodeinone dimethyl ketal by the general method of Example 8, and was recrystallised from diethyl ether/petrol ether to give 14-β-acetylamino-7,8-dihydrocodeinone as colourless needle shaped crystals, m.p. 198°–199.5°.

EXAMPLE 12

14-β-Aminocodeine

A solution of 14-β-aminocodeinone in methanol was treated portionwise with sodium borohydride at room temperature. Removal of the solvent from the cooled reaction mixture gave 14-β-aminocodeine. m.p. 185°–186°.

EXAMPLE 13

14-β-Allylaminocodeinone

A solution of 14-β-amino-(N-benzyloxycarbonyl)-norcodeinone dimethyl ketal in acetone was alkylated with allyl iodide using the method of Example 5, and the intermediate product was used as below without further purification.

A solution of the above intermediate (13.0 g) in THF (50 ml) was added dropwise over 5 min to an ice-cold stirred suspension of LiAlH₄ (6.5 g) in THF (100 ml) and the resulting mixture was stirred at room temperature for 24 hr. The excess LiAlH₄ was decomposed by the cautious addition of a saturated solution of sodium sulphate and the aluminium salts removed by filtration, washed well with CHCl₃, and the combined filtrates evaporated to small bulk. The resulting oil was acidified 2 N HCl (50 ml) and stood for 2 hr. The mixture was neutralised, extracted with CHCl₃, the extracts washed, dried and evaporated to give a brown oil, which was passed down a short column of grade III alumina, and the pale yellow eluents were evaporated to give a yellow oil which crystallised upon trituration with diethyl ether. The resultant crystalline solid was collected by filtration, washed with diethyl ether, and recrystallised fron acetone/petroleum ether (60°–80°) to give colourless needles (3.89 g), mp 171°–172.5°.

EXAMPLE 14

14-β-(5'-Phenylpent-4'-enyl)aminocodeinone (a) A solution of 5-phenylpent-4-enoic acid (5 g) in CHCl₃ was treated with triethylamine (6.3 g), cooled to −30°, treated with isobutyl chloroformate (4.27 g) and the resulting solution stirred at −20° for 5 min. The solution was then treated with a solution of 14-β-aminocodeinone dimethyl ketal (10.8 g) in CHCl₃ (50 ml) and the solution allowed to warm to room temperature and stirred for one hour. The solution was shaken with water (2×), the chloroform layer separated, dried, and evaporated to give a yellow oil, which crystallised upon trituration with petroleum ether. The solid was collected and dried.

(b) The above material was reduced by the method of Example 4.

EXAMPLE 15

14-β-Pentanoylaminocodeinone

A solution of 14-β-aminocodeinone dimethyl ketal (5.0 g) in CHCl₃ (100 ml) and triethylamine (5 ml) was cooled to 0°, treated with pentanoyl chloride (1.9 g) and allowed to warm to room temperature over 1 hour. The solution was washed with water, evaporated to small bulk, dissolved in THF (50 ml) treated with 2 N HCl (50 ml) and stood for 2 hr. The mixture was neutralised, extracted with CHCl₃, the extracts washed, dried and evaporated to give a colourless solid which was recrystallised from an acetone/di-isopropyl ether mixture to give the product as colourless plates, m.p. 213°–217°.

EXAMPLE 16

14-β-p-Hydroxycinnamoylaminocodeinone

A solution of 14-β-aminocodeinone dimethyl ketal (3 g) in CHCl₃ (60 ml) and triethylamine (3 ml) was treated with p-acetoxycinnamoyl chloride [freshly prepared from the acid (1.68 g) and thionyl chloride], and the solution stirred at room temperature for 2 hr. The solvents were removed by evaporation, and the oily residue dissolved in conc. HCl and the solution heated on the steam bath for 10 min. The bright orange/yellow solution was diluted with water, neutralised with NaHCO₃, extracted with methanol/CHCl₃ (1:1), and the combined extracts dried and evaporated. The resulting bright yellow solid was recrystallised from methanol to give the desired product (1.61 g) as bright yellow needles, m.p. 316°–317°.

EXAMPLE 17

14-β-(Pent-2-enoyl)aminocodeinone

The desired product was prepared by a mixed anhydride reaction from pent-2-enoic acid and 14-β-aminocodeinone dimethyl ketal using the general method of Example 14a, and the hydrolysis to the corresponding codeinone was performed using the general method for acid hydrolysis outlined in Example 15. Product recrystallised from aqueous ethanol had m.p. 224°–226°.

EXAMPLE 18

14-β-Dimethylaminocodeinone (a) A solution of 14-β-amino-(N-benzyloxycarbonyl)-norcodeinone dimethyl ketal in acetone was alkylated with a large excess of methyl iodide using the method of Example 5. After a period of 36 hr, the mixture was diluted with water, extracted with chloroform, the extracts washed, dried, and evaporated. The resulting pale yellow oil crystallised upon trituration with ether, and the resultant solid 14-β-dimethylamino-(N-benzyloxycarbonyl)norcodeinone dimethyl ketal, was used without further purification.

(b) Reduction of this material was carried out with LiAlH₄ using the general method of Example 3 followed by acid hydrolysis using the same general procedure giving 14-β-dimethylaminocodeinone as plates from cyclohexane, m.p. 205°–207.5°.

EXAMPLE 19

14-β-Hexanoylamino-(N-benzyl)norcodeinone (a) A solution of 14-β-amino-(N-benzyloxycarbonyl)-norcodeinone dimethyl ketal was acylated with hexanoyl chloride in a solution of chloroform/triethylamine by heating to reflux 24 hr. The reaction mixture was washed with water, dried, and evaporated to give a red oil. The mixture was purified by chromatography on silica gel, and the 14-β-hexanoylamino-(N-benzyloxycarbonyl)norcodeinone dimethyl ketal was hydrolysed by aqueous acid in THF solution, to give the corresponding codeinone as a colourless oil.

(b) A solution of the above material in ethyl acetate/acetic acid (5:1) was hydrogenated for 48 hr, over 10% Pd/C. The solvents were removed, the mixture neutralised, extracted with chloroform, the extracts dried and evaporated to give a colourless oil, which crystallised upon trituration with ether to give a colourless solid which was used without further purification.

(c) A solution of 14-β-hexanoylamino-norcodeinone was alkylated using the method of Example 5 with benzyl bromide, to give 14-β-hexanoylamino-(N-benzyl)norcodeinone as needles from ethanol, m.p. 206°–210°.

EXAMPLE 20

14-β-Hexanoylamino[N-(2-phenethyl)]-norcodeinone

This was prepared by an analogous method to Example 19 as platelets from aqueous ethanol, m.p. 163°–166°.

Table 1 describes the preparation of further compounds of the formula:

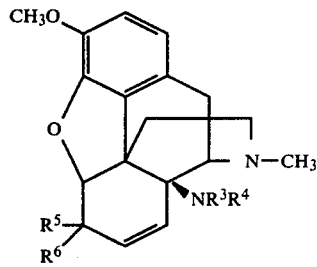

prepared by the methods of the above examples, the final column of the Table giving the solvent of recrystallisation.

TABLE 1

| Example | $R^3$ | $R^4$ | $R^5$ | $R^6$ | Method | m.p. °C. | Solvent |
|---|---|---|---|---|---|---|---|
| 21 | n-$C_3H_7$ | H | =O | | 3 | 137–138 | E/P |
| 22 | n-$C_4H_9$ | H | =O | | 3 | 141–144 | P |
| 23 | n-$C_5H_{11}$ | H | =O | | 3 | 122–122.5 | P |
| 24 | n-$C_6H_{13}$ | H | =O | | 3 | 137–139.5 | E/P |
| 25 | n-$C_{10}H_{21}$ | H | =O | | 4 | 72–76 | P |
| 26 | n-$C_{12}H_{25}$ | H | =O | | 4 | 191–195* | A/M/E |
| 27 | i-$C_4H_9$ | H | =O | | 3 | 177–181 | P |
| 28 | $CH_2Ph$ | H | =O | | 3 | 163.5–165 | H |
| 29 | $(CH_2)_2Ph$ | H | =O | | 3 | 194–197 | P |
| 30 | $(CH_2)_3Ph$ | H | =O | | 3 | 124–125 | P |
| 31 | H | $COC_5H_{11}$ | =O | | 7 | 209.5–212 | A/DIPE |
| 32 | H | $COC_6H_{13}$ | =O | | 7 | 175–178 | E/P |
| 33 | H | $COC_9H_{19}$ | =O | | 8 | 174–177.5 | A/DIPE |
| 34 | H | $COC_{11}H_{23}$ | =O | | 8 | 157–158 | A/DIPE |
| 35 | H | COPh | =O | | 8 | 152–155 | A/DIPE |
| 36 | H | $CO(CH_2)_2Ph$ | =O | | 8 | 190–191 | E/P |
| 37 | n-$C_7H_{15}$ | H | =O | | 4 | 107–107.5 | P |
| 38 | n-$C_8H_{17}$ | H | =O | | 4 | 164–167* | M/E |
| 39 | $CH_2$-c-$C_7H_{13}$ | H | =O | | 4 | 125–126 | Et/W |
| 40 | $CH_2$-c-$C_8H_{15}$ | H | =O | | 4 | 132–133 | P/A |
| 41 | $CH_2CH_2$-c-$C_3H_5$ | H | =O | | 4 | 151–152 | P |
| 42 | $(CH_2)_4Ph$ | H | =O | | 4 | 96–98 | P |
| 43 | $(CH_2)_5Ph$ | H | =O | | 4 | 237–237.5* | M/A/E |
| 44 | $(CH_2)_6Ph$ | H | =O | | 4 | 150–152* | M/E |
| 45 | $(CH_2)_3$—$C_6H_4$(4-Cl) | H | =O | | 4 | 135–136.5 | P |
| 46 | $(CH_2)_3$—$C_6H_4$(4-Me) | H | =O | | 4 | 164.5–165.5 | A/P |
| 47 | $(CH_2)_3$—$C_6H_4$(4-OMe) | H | =O | | 4 | 126–128 | E/P |
| 48 | $CH_2CH=CHCH_3$ | H | =O | | 5 | 112–114.5 | P |
| 49 | $(CH_2)_3CH=CH_2$ | H | =O | | 4 | 126–127 | P |
| 50 | $(CH_2)_3CH=CHCH_3$ | H | =O | | 4 | 117–119 | P |
| 51 | $CH_2CH=CHPh$ | H | =O | | 5 | 184–188 | A/CH |
| 52 | H | $COC_7H_{15}$ | =O | | 15 | 160–161.5 | A/DIPE |
| 53 | H | $COC(CH_3)_3$ | =O | | 15 | 196–197 | DIPE/P |
| 54 | H | $COCH_2C(CH_3)_3$ | =O | | 15 | 233.5–234.5 | DIPE/A |
| 55 | H | CO-c-$C_7H_{13}$ | =O | | 15 | 284–285 | Et |
| 56 | H | CO-c-$C_8H_{15}$ | =O | | 15 | 284–286 | Et |
| 57 | H | $COCH_2$-c-$C_3H_5$ | =O | | 15 | 228–230 | Et/W |
| 58 | H | $COCH_2Ph$ | =O | | 15 | 241–242 | Et/W |
| 59 | H | $CO(CH_2)_3Ph$ | =O | | 15 | 197–199 | A/E/P |
| 60 | H | $CO(CH_2)_4Ph$ | =O | | 15 | 176–177 | DIPE/A |
| 61 | H | $CO(CH_2)_5Ph$ | =O | | 15 | 178.5–180 | Et/W |
| 62 | H | $CO(CH_2)_2$—$C_6H_4$(4-Cl) | =O | | 15 | 245–249 | A/DIPE |
| 63 | H | $CO(CH_2)_2$—$C_6H_4$(4-Me) | =O | | 15 | 240–242.5 | A/DIPE |
| 64 | H | $CO(CH_2)_2$—$C_6H_4$(4-OMe) | =O | | 15 | 200.5–202 | Et/W |
| 65 | H | COCH=CH—$C_6H_4$(4-Cl) | =O | | 15 | 279–281.5 | A/DIPE |
| 66 | H | COCH=CH—$C_6H_4$(4-Me) | =O | | 15 | 289.5–291 | A/DIPE |
| 67 | H | COCH=CH—$C_6H_4$(4-OMe) | =O | | 15 | 256.5–258 | Et |
| 68 | H | COCH=CH—$C_6H_3$(3,4-Cl) | =O | | 15 | 242–244 | Et |
| 69 | H | $COCH=CH_2$ | =O | | 15 | 113–115 | Et/W |

TABLE 1-continued

| Example | R³ | R⁴ | R⁵ | R⁶ | Method | m.p. °C | Solvent |
|---|---|---|---|---|---|---|---|
| 70 | H | COCH=CHCH₃ | | =O | 15 | 234–235 | E/P |
| 71 | H | COCH=C(CH₃)₂ | | =O | 15 | 170–172 | Et/W |
| 72 | H | CO(CH₂)₂CH=CH₂ | | =O | 15 | 206–208 | Et/W |
| 73 | H | CO(CH₂)₂CH=CHCH₃ | | =O | 15 | 218–220 | Et/W |
| 74 | H | COCH₂CH=CHPh | | =O | 15 | 228–233 | A/DIPE |
| 75 | H | CO(CH₂)₂CH=CHPh | | =O | 17 | 187–189 | Et/W |
| 76 | H | CO—C₆H₄(4-Me) | | =O | 15 | 260–262 | E |

EXAMPLE 77

14-β-Aminomorphinone (a) Boron tribromide (3.0 ml) was added dropwise to a stirred solution of 14-β-aminocodeinone dimethyl ketal (2.0 g) in methylene chloride (60 ml) at −78° and after 5 minutes at −78° the reaction mixture was warmed to −15° and then kept at −10° for 1 hour. The reaction mixture was diluted with methanol (10 ml) and the solution poured onto excess sodium hydroxide solution at 0°. The organic layer was separated, washed with sodium hydroxide and discarded. The combined aqueous solutions were acidified with dilute hydrochloric acid, the pH adjusted to 7.0 with sodium bicarbonate and the aqueous solution extracted with chloroform. The combined extracts were dried and evaporated to give a tan coloured solid (1.25 g) which was recrystallised from chloroform/petrol ether to give 14-β-aminomorphinone as colourless needles, m.p. >350°.

(b) (i) A solution of 14-β-nitrocodeinone or the corresponding dimethyl ketal in methylene chloride was cooled to −60°, treated with BBr₃ and stirred at −20° to −30° for 1 hour. The reaction mixture was treated with methanol, and poured into dilute sodium hydroxide solution, which was neutralised by passage of CO₂ gas, and then extracted with methylene chloride. Evaporation of the extracts gave an orange yellow gum which was recrystallised from diethyl ether/petrol ether to give pale yellow needle shaped crystals, m.p. 200° with decomposition.

(ii) A solution of 14-β-nitromorphinone in methanol was treated with an aqueous suspension of sodium dithionite (excess) and the resulting mixture was heated to gentle reflux overnight. Removal of the solvent, extraction of the reaction residue and evaporation of the extracts gave 14-β-aminomorphinone identical to that described in (a) above.

EXAMPLE 78

14-β-Methylaminomorphinone

A solution of 14-β-methylaminocodeinone (0.70 g) in methylene chloride (60 ml) was cooled to −60°, treated with boron tribromide (2.5 ml) and then stirred at −20° to −30° for 2 hours. The reaction mixture was diluted with methanol (10 ml), poured onto dilute sodium hydroxide solution sufficient to basify it, stirred for 5 minutes, back acidified with concentrated hydrochloric acid, and the pH adjusted to 7.0 with sodium bicarbonate. The resulting solution was extracted with a mixture of chloroform and methanol (3:1), and the organic extracts dried, and the solvent removed in vacuo. The resulting solid was purified by passage down a short column of grade III alumina eluting with a mixture of chloroform/methanol (5:1) and the eluents were evaporated to give a solid which on crystallisation from chloroform/petrol ether gave 14-β-methylaminomorphinone (0.29 g, 44%), as pale yellow needle shaped crystals, m.p. 250°–252° (with decomposition).

EXAMPLE 79

14-β-Pentanoylamino-7,8-dihydromorphinone

A solution of 14-β-pentanoylaminomorphinone (1.5 g) in methanol (60 ml) was hydrogenated at atmospheric pressure over 10% Pd/C (300 mg). After uptake of H₂ ceased, the catalyst was removed by filtration, the residual oil dissolved in ether, treated with a saturated solution of HCl/ether to precipitate the HCl salt, which was collected by filtration, and recrystallised from methanol/diethyl ether as a colourless crystalline solid (1.03 g), m.p. 199°–200°.

EXAMPLE 80

14-β-Hexanoylamino-(N-benzyl)normorphinone

The dealkylation of the corresponding codeinone was carried out using the method of Example 78, and was obtained as a colourless powder by recrystallisation from ether/petroleum ether, m.p. 108°–110° (a glassy melt).

EXAMPLE 81

14-β-Hexanoylamino-[N-(2-phenethyl)]-normorphinone

The dealkylation of the corresponding codeinone was carried out using the method of Example 78, and was obtained as a colourless powder by recrystallisation from ether/petroleum ether which gave a glassy form upon removal of solvent at 80°, m.p. 94°–96° (a glassy melt).

EXAMPLE 82

14-β-Methylaminomorphinone

This was prepared by the method of Example 78, using boron trichloride, and stirred at 0° to 10°, for 2 hours. Work up of the reaction mixture gave a product identical (tlc. ir. m.p.) to that of Example 78.

Table 2 describes the preparation of further compounds of the formula:

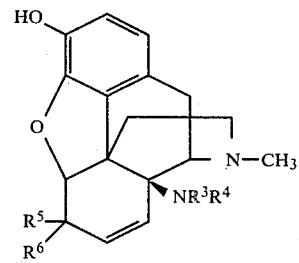

prepared by the method of Example 78, the final column of the Table giving the solvent of recrystallisation.

TABLE 2

| Example | $R^3$ | $R^4$ | $R^5$ | $R^6$ | m.p. °C. | Solvent |
|---|---|---|---|---|---|---|
| 83 | n-$C_3H_7$ | H | = | O | 110-112 | CH |
| 84 | n-$C_6H_{13}$ | H | = | O | 175-178 d | CH |
| 85 | i-$C_4H_9$ | H | = | O | 181-183 | CH |
| 86 | $CH_2$-c-$C_3H_5$ | H | = | O | 193-196 | DCM/P |
| 87 | $(CH_2)_3Ph$ | H | = | O | 91-93 | CH/P |
| 88 | H | CHO | = | O | >300 | DCM/Et/P |
| 89 | H | $COCH_3$ | = | O | >300 | DCM/P |
| 90 | H | $CO(CH_2)_2Ph$ | = | O | 156-157 | A/P |
| 91 | H | COCH=CHPh | = | O | 197-200 | A/P |
| 92 | H | $COCH_3$ | = | OΔ | 260-280 d | Et |
| 93 | H | CO—◁ | = | O | 246-260 | DCM/P |
| 94 | n-$C_4H_9$ | H | = | O | 112-114 | CH |
| 95 | n-$C_5H_{11}$ | H | = | O | 189.5-191 | A/CH |
| 96 | n-$C_7H_{15}$ | H | = | O | 88-90 | CH |
| 97 | n-$C_8H_{17}$ | H | = | O | 73-77 | CH/P |
| 98 | $CH_2Ph$ | H | = | O | 212-214 | CH |
| 99 | $CH_2CH_2Ph$ | H | = | O | 196-197 | CH/A |
| 100 | $(CH_2)_4Ph$ | H | = | O | 162-163** | M/E |
| 101 | $(CH_2)_5Ph$ | H | = | O | 147-148** | M/E |
| 102 | $(CH_2)_6Ph$ | H | = | O | 151-152** | M/E |
| 103 | $CH_2CH=CH_2$ | H | = | O | 167-168.5 | CH |
| 104 | $CH_2CH=CHCH_3$ | H | = | O | 100-104 | CH |
| 105 | $(CH_2)_3CH=CH_2$ | H | = | O | 202-203 | A/CH |
| 106 | $(CH_2)_3CH=CHCH_3$ | H | = | O | 94-96 | CH |
| 107 | $CH_2CH=CHPh$ | H | = | O | 235-236 | CH |
| 108 | $(CH_2)_3CH=CHPh$ | H | = | O | 175-177* d | M/E |
| 109 | $(CH_2)_3$—$C_6H_4$(4-Me) | H | = | O | 117-119 | CH |
| 110 | $(CH_2)_3$—$C_6H_4$(4-Cl) | H | = | O | 125-127 | CH |
| 111 | $(CH_2)_3$—$C_6H_4$(4-OH) | H | = | O | 94-96 | E/P |
| 112 | $CH_2CH_2$-c-$C_3H_5$ | H | = | O | 196-197.5 | CH |
| 113 | $CH_2$-c-$C_7H_{13}$ | H | = | O | 195-196 | CH |
| 114 | $CH_2$-c-$C_8H_{15}$ | H | = | O | 197-199 | Et/W |
| 115 | H | $COC_3H_7$ | = | O | 145-147 | A/P |
| 116 | H | $COC_4H_9$ | = | O | 141-143 | A/P |
| 117 | H | $COC_5H_{11}$ | = | O | 160-162 | A/P |
| 118 | H | $COC_6H_{13}$ | = | O | 153-155 | A/P |
| 119 | H | $COC_7H_{15}$ | = | O | 198-202 | A/P |
| 120 | H | $COC_9H_{19}$ | = | O | 141-143 | A/P |
| 121 | H | $COC_{11}H_{23}$ | = | O | 109-110 | A/P |
| 122 | H | COPh | = | O | 250-252 | E/P |
| 123 | H | CO—$C_6H_4$(4-ME) | = | O | 166-168 | Et/W |
| 124 | H | $COCH_2Ph$ | = | O | 270-272 | Et/W |
| 125 | H | $CO(CH_2)_3Ph$ | = | O | 231-233 | Et |
| 126 | H | $CO(CH_2)_4Ph$ | = | O | 200-202 | Et |
| 127 | H | $CO(CH_2)_5Ph$ | = | O | 176-177 | CH |
| 128 | H | $COCH=CH_2$ | = | O | 267-269 | E/P |
| 129 | H | $COCH=CHCH_3$ | = | O | 285-286 | E/P |
| 130 | H | $COCH=C(CH_3)_2$ | = | O | 148-150 | E/P |
| 131 | H | $CO(CH_2)_2CH=CH_2$ | = | O | 131-133 | E/P |
| 132 | H | $COCH=CHCH_2CH_3$ | = | O | 225-227 | E/P |
| 133 | H | $CO(CH_2)_2CH=CHCH_3$ | = | O | 117-119 | E/P |
| 134 | H | $COCH_2CH=CHPh$ | = | O | 134-139 | Et/W |
| 135 | H | $CO(CH_2)_2CH=CHPh$ | = | O | 139-141 | E/P |
| 136 | H | COCH=CH—$C_6H_4$(4-Cl) | = | O | 302-304 | Et/W |
| 137 | H | COCH CH—$C_6H_4$(4-Me) | = | O | 274-276 | Et/W |
| 138 | H | COCH=CH—$C_6H_4$(4-OH) | = | O | 240-242 | B/M |
| 139 | H | $COCH_2CH_2$—$C_6H_4$(4-Cl) | = | O | 277-279 | Et/W |
| 140 | H | $COCH_2CH_2$—$C_6H_4$(4-Me) | = | O | 143-145 | Et/W |
| 141 | H | $COCH_2CH_2$—$C_6H_4$(4-OH) | = | O | 260-261 | B/M |
| 142 | H | COCH=CH—$C_6H_3$(3,4-Cl) | = | O | 195-197 | E/P |
| 143 | H | $COC(CH_3)_3$ | = | O | 269-270 | E/P |
| 144 | H | $COCH_2C(CH_3)_3$ | = | O | 209-210 | Et/W |
| 145 | H | $COCH_2$-c-$C_3H_5$ | = | O | 270-272 | Et/W |
| 146 | H | CO-c-$C_7H_{13}$ | = | O | 278-280 | Et/W |
| 147 | H. | CO-c-$C_8H_{15}$ | = | O | 278-280 | Et/W |
| 148 | H | $COC_6H_{13}$ | = | OΔ | 198-199* | M/E |
| 149 | H | $COC_6H_{13}$ | H | OH | 232-238* d | M/E |
| 150 | H | $COC_5H_{11}$ | H | OH | 259-265* d | M/E |
| 151 | $CH_3$ | $CH_3$ | = | O | 225-226 | CH |
| 152 | $C_{10}H_{21}$ | H | = | O | 175-178* | M/E |

TABLE 2-continued

| Example | R³ | R⁴ | R⁵ | R⁶ | m.p. °C. | Solvent |
|---|---|---|---|---|---|---|
| 153 | $C_{12}H_{25}$ | H | | =O | 143–145* | M/E |

Δ 7,8-Dihydro
*hydrochloride
**dihydrochloride
d decomposition
Solvents of crystallisation
A - acetone
C - chloroform
CH - cyclohexane
DCM - Dichloromethane
E - Diethyl ether
Et - Ethanol
P - Petroleum ether
W - Water
M - Methanol
DIPE - Di-iso-propyl ether
H - Hexane
B - n-Butanol The compounds of the invention exhibit pharmacological actions mediated by opiate receptors. They have activity when tested in the transmurally stimulated mouse vas deferens described by Henderson, G., Hughes, J., Kosterlitz, H, (Brit. J. Pharmacol. 46, 764, [1972]).

In the above mentioned test method of Henderson et al male albino mice (OLA MFI strain) are killed by a blow on the head and the vasa deferentia removed and set up in an isolated organ bath of 2½ ml volume. A 'twitch' response is produced by low frequency (0.1 Hz) stimulation with 0.1 msec rectiliniar pulses. The response is depressed by a large number of different pharmacologically active agents (local anaesthetics, smooth muscle depressants, adrenergic neuron blocking agents, presynaptic α-receptor stimulants, β-stimulants and narcotic agonists) but it is possible to differentiate between depression of twitch produced by narcotic agonists and depression produced by other mechanisms, by repeating the test in the presence of the narcotic antagonist naloxone (The test has been shown to be an extremely specific method of detecting narcotic agonist and antagonist activity [Hughes J, Kosterlitz H, Leslie F. M., Brit. J. Pharmacol 51, 139–140]).

A test compound is dissolved in distilled water to produce a stock solution of concentration 1 mg/ml. Serial dilutions are carried out using Krebs solution to produce concentrations of 10 µg, 1 µg and 0.1 µg/ml. The compound is tested by adding between 0.1–0.3 ml of the solutions to the organ bath. A dose response curve is then drawn and compared with that for normorphine.

The compounds have also been screened for narcotic agonist activity in the rat using tail pressure as the nociceptive stimulus as described by Green, H. F., and Young P. A., Br. J. Pharmac. Chemother, 6, 572, (1951). Compounds exhibiting activity in this antinociceptive test are agonists at the opiate receptor population and may have clinical utility inter alia as analgesics, neuroleptanalgesics and anti-diarrhoeal agents. In the above agonist test, the compound of Example 84 when administered subcutaneously had an $ED_{50}$ of 0.00053 mg/Kg. (In this test, morphine [S.C.] had an $ED_{50}$ of 0.66 mg/Kg).

The therapeutic compositions may be in a form suitable for oral, rectal or parenteral administration. Such oral compositions may be in the form of capsules, tablets, granules or liquid preparations such as elixirs, syrups or suspensions.

Tablets contain as active ingredient a compound of Formula I (or a pharmaceutically acceptable salt thereof) in admixture with excipients which are suitable for the manufacture of tablets. These excipients may be inert diluents such as calcium phosphate, microcrystalline cellulose, lactose, sucrose or dextrose; granulating and disintegrating agents such as starch; binding agents such as starch, gelatine, polyvinylpyrrolidone or acacia; and lubricating agents such as magnesium stearate, stearic acid or talc.

Compositions in the form of capsules may contain the active ingredient mixed with an inert solid diluent such as calcium phosphate, lactose or kaolin in a hard gelatine capsule.

Compositions for rectal administration in the form of suppositories may contain in addition to the active ingredient excipients such as cocoa butter or a suppository wax.

Compositions intended for parenteral administration may be in the form of a sterile preparation such as solutions in for example water, saline, buffered saline or polyhydroxy alcohols such as propylene glycol or polyethyleneglycols.

For the purposes of convenience and accuracy of dosing the compositions are advantageously employed in unit dosage form. For oral administration the unit dosage form may contain 0.1 to 10 mg, of the compound of Formula I or an equivalent amount of a pharmaceutically acceptable salt thereof. Parenteral unit dosage form may contain from 0.01 mg to 10 mg of the said compound (or salt thereof) per 1 ml of the preparation.

We claim:

1. A compound of the general formula:

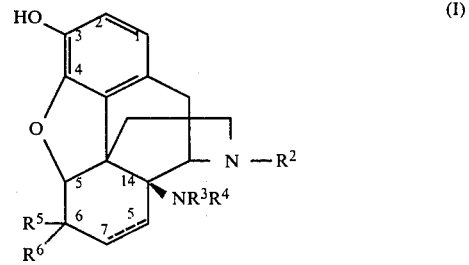

wherein
$R^2$ is methyl or Ar-alkyl $C_{1-5}$;
$R^3$ is hydrogen, alkyl $C_{1-12}$, alkenyl $C_{3-8}$, cycloalkyl $C_{3-7}$ alkyl $C_{1-4}$, Ar-alkyl $C_{1-5}$ or Ar-alkenyl $C_{3-5}$, provided that $R^3$ does not contain the system —CH=CH— attached to the nitrogen atom at position 14;

$R^4$ is hydrogen, alkyl $C_{1-8}$ or the group $COR^7$ in which $R^7$ is hydrogen, alkyl $C_{1-11}$, alkenyl $C_{2-7}$, Ar, Ar-alkyl $C_{1-5}$, Ar-alkenyl $C_{2-5}$, cycloalkyl $C_{3-8}$ or cycloalkyl $C_{3-8}$ alkyl $C_{1-3}$;

Ar is phenyl or phenyl subtituted by halogen, alkyl $C_{1-3}$, hydroxy or alkoxy $C_{1-3}$;

$R_5$ is hydrogen and $R^6$ is hydroxy; or $R^5$ and $R^6$ are together oxygen;

the dotted line indicates an optional bond; and its pharmaceutically acceptable salts.

2. The compound of claim 1 which is 14-β-aminomorphinone.

3. The compound of claim 1 which is 14-β-pentanoylaminomorphinone.

4. The compound of claim 1 which is 14-β-hexanoylaminomorphinone.

5. The compound of claim 1 which is 14-β-heptanoylaminomorphinone.

6. The compound of claim 1 which is 14-β-octanoylaminomorphinone.

7. The compound of claim 1 which is 14-β-butylaminomorphinone.

8. The compound of claim 1 which is 14-β-pentylaminomorphinone.

9. The compound of claim 1 which is 14-β-hexylaminomorphinone.

10. The compound of claim 1 which is 14-β-heptylaminomorphinone.

11. The compound of claim 1 which is 14-β-octylaminomorphinone.

12. A process for the preparation of a compound as claimed in claim 1 which process comprises treating a compound of the general Formula II:

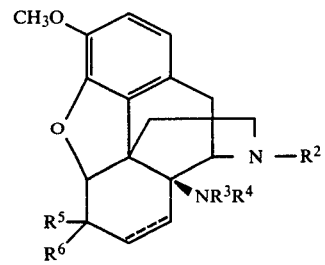

(II)

in which $R^2, R^3, R^4, R^5, R^6$ and the dotted line are as defined in claim 1. with boron tribromide at a temperature in the range of from $-30°$ to $-10°$ C.

13. A process for the preparation of a compound of Formula I as claimed in claim 1 wherein $R^5$ and $R^6$ are together oxygen which process comprises treating the compound of the general Formula II in which $R^2, R^3, R^4$ and the dotted line are as defined in claim 1 and in which both $R^5$ and $R^6$ are methoxy, with boron tribromide at a temperature in the range of from $-30°$ to $-10°$ C.

14. A process for the preparation of 14-β-aminomorphinone which process comprises treating 14-β-nitrocodeinone or its dimethyl ketal in methylene chloride with boron tribromide at a temperature in the range of from $-30°$ to $-10°$ C., and reducing the resultant 14-β-nitromorphinone with sodium dithionite.

15. A pharmaceutical composition for the relief of pain which comprises at least one compound as claimed in claim 1, or a pharmaceutically acceptable salt thereof, together with a pharmaceutically acceptable diluent or carrier.

16. A pharmaceutical composition for the relief of pain according to claim 15 in unit dosage form for oral administration which contains from 0.1 to 10 mg of the said compound or salt thereof per unit dosage.

17. A pharmaceutical composition for the relief of pain according to claim 16 in unit dosage form for parenteral administration which contains from 0.1 to 10 mg of the said compound or salt thereof per 1 ml of the composition.

* * * * *